United States Patent
Rathjen

(10) Patent No.: US 9,248,047 B2
(45) Date of Patent: Feb. 2, 2016

(54) SYSTEM FOR PROTECTING TISSUE IN THE TREATMENT OF EYES

(75) Inventor: Christian Rathjen, Bremen (DE)

(73) Assignee: ZIEMER HOLDING AG (CH)

( * ) Notice: Subject to any disclaimer, the term of this patent is extended or adjusted under 35 U.S.C. 154(b) by 905 days.

(21) Appl. No.: 11/654,603

(22) Filed: Jan. 18, 2007

(65) Prior Publication Data

US 2007/0173793 A1    Jul. 26, 2007

Related U.S. Application Data

(60) Provisional application No. 60/760,931, filed on Jan. 23, 2006.

(30) Foreign Application Priority Data

Sep. 12, 2006 (EP) .................................... 06405392

(51) Int. Cl.
*A61B 18/18* (2006.01)
*A61F 9/008* (2006.01)
(Continued)

(52) U.S. Cl.
CPC ............... *A61F 9/008* (2013.01); *A61F 9/0084* (2013.01); *A61F 9/00825* (2013.01); *A61B 18/20* (2013.01);
(Continued)

(58) Field of Classification Search
CPC . A61F 9/008; A61F 9/00825; A61F 9/00824; A61F 2009/00844; A61F 2009/00872; A61F 2009/00897; A61B 18/20; A61B 2018/00636
USPC ............. 606/107, 166, 4–6; 600/405; 607/53; 128/898
See application file for complete search history.

(56) References Cited

U.S. PATENT DOCUMENTS 5,348,551 A * 9/1994 Spears et al. ....................... 606/5
5,395,356 A * 3/1995 King et al. ........................ 606/4
(Continued)

FOREIGN PATENT DOCUMENTS

DE    102007017599    10/2008
EP    1430829    6/2004
(Continued)

OTHER PUBLICATIONS

Intraocular Photodisruption with Picosecond Laser Pulses: Tissue Effects in Cornea, Lens and Retina; Vogel et al., Investigative Ophthalmology & Visual Science, Jun. 1994.*
(Continued)

*Primary Examiner* — Gary Jackson
*Assistant Examiner* — Boniface N Nganga
(74) *Attorney, Agent, or Firm* — Ostrolenk Faber LLP

(57) ABSTRACT

To protect tissue in the treatment of an eye (3) with a focused pulsed laser beam (21) generated by a laser system (2), e.g. a femtolaser system, operating data which define an operating area operated on by the focus (F) of the laser beam (21) during the treatment are acquired in a device (1). The device (1) comprises a processing module (14) for providing control data for the laser system (2) on the basis of the operating data and taking into consideration the light propagation in the eye. The control data limit the time of the treatment by the focus (F) at positions within the operating area in each case in such a manner that tissue damage resulting from the treatment by the laser beam (21) is essentially prevented in eye structures located outside the operating area. In particular, the control data determine movements of the focus (F) within the operating area and/or the activity of the laser beam (21) in such a manner that the mean irradiation intensity is reduced and the maximum temperatures in the tissue of eye structures located outside the operating area, particularly in the iris and the retina, are reduced.

21 Claims, 4 Drawing Sheets

(51) Int. Cl.
*A61B 18/20* (2006.01)
*A61B 18/00* (2006.01)

(52) U.S. Cl.
CPC .............. *A61B 2018/00636* (2013.01); *A61F 2009/00844* (2013.01); *A61F 2009/00872* (2013.01); *A61F 2009/00897* (2013.01)

(56) References Cited

U.S. PATENT DOCUMENTS

| | | | |
|---|---|---|---|
| 5,886,468 A | 3/1999 | Terada et al. | |
| 5,984,916 A | 11/1999 | Lai | |
| 6,676,279 B1* | 1/2004 | Hubbell et al. | 362/293 |
| 6,702,806 B2* | 3/2004 | Gray et al. | 606/5 |
| 6,726,680 B1* | 4/2004 | Knopp et al. | 606/12 |
| 7,673,991 B2* | 3/2010 | Van den Berg et al. | 351/221 |
| 2002/0171804 A1 | 11/2002 | Rathjen | |
| 2003/0028115 A1* | 2/2003 | Thomas | 600/476 |
| 2003/0040738 A1* | 2/2003 | Ruiz et al. | 606/5 |
| 2003/0160943 A1 | 8/2003 | Xie et al. | |
| 2003/0223037 A1* | 12/2003 | Chernyak | 351/209 |
| 2004/0039378 A1* | 2/2004 | Lin | 606/6 |
| 2004/0059321 A1* | 3/2004 | Knopp et al. | 606/10 |
| 2004/0073245 A1* | 4/2004 | Schachar et al. | 606/166 |
| 2004/0111083 A1* | 6/2004 | Gross et al. | 606/5 |
| 2004/0199149 A1 | 10/2004 | Myers et al. | |
| 2004/0243112 A1* | 12/2004 | Bendett et al. | 606/5 |
| 2005/0024586 A1 | 2/2005 | Teiwes et al. | |
| 2005/0165386 A1* | 7/2005 | Kurtz et al. | 606/4 |
| 2007/0213693 A1* | 9/2007 | Plunkett | 606/6 |
| 2007/0273611 A1 | 11/2007 | Torch | |
| 2010/0195876 A1* | 8/2010 | Artal Soriano et al. | 382/128 |

FOREIGN PATENT DOCUMENTS

| | | |
|---|---|---|
| EP | 2020205 | 2/2009 |
| WO | WO 03/032803 A2 | 4/2003 |
| WO | WO 03/082162 A2 | 10/2003 |
| WO | WO03101355 | 12/2003 |

OTHER PUBLICATIONS

Experimental Ocular Surgery with a High-Repetition Rate Erbium:YAG laser; Brazitilos et al., Investigative Ophthalmology & Visual Science, Aug. 1998.*

* cited by examiner

SYSTEM FOR PROTECTING TISSUE IN THE TREATMENT OF EYES

TECHNICAL FIELD

The present invention relates to a device and a method for protecting tissue in the treatment of eyes. In particular, the present invention relates to a device and a method for protecting tissue in the treatment of an eye with a focused pulsed laser beam generated by a laser system.

PRIOR ART

Femtolaser systems which have pulse widths of typically 10 fs to 1000 fs (1 fs=$10^{-15}$ s) have the special feature that it is also possible to operate on transparent materials in the focus by means of nonlinear absorption and subsequent interaction (e.g. photodisruption). In particular, the operative cutting in the cornea introduced into practical use shall be mentioned as an example. WO 03/032803 describes a system suitable for this purpose with a closed feedback loop for positioning the focused laser beam. A significant feature of femtolaser systems is the possibility of freely guiding the focus in the material which enables any cutting patterns to be generated. U.S. Pat. No. 5,984,916 describes an example of a femtolaser system for the surgical treatment of eye tissue. In US 2004/0199149, interaction zones deviating from cuts are described.

In general, the nonlinear absorption is not complete as a result of which a part of the irradiated energy is always transmitted when operating on transparent materials. In the eye, in particular, this energy is absorbed by tissue layers lying underneath. Strong absorption takes place due to the high proportion of pigments in the retina and the iris.

The fact that laser systems are programmable freely or within limits combined with only partial absorption can cause damage of underlying areas of material or tissue layers in the case of inexpert operation (e.g. programming). At the eye, e.g. damage due to phototoxicity in the shortwave visible wavelengths and photocoagulation (photothermal effect over the entire range of wavelengths) is known. For example, a combination of both effects can occur when infrared light is used: phototoxicity due to the generation of white light in the focus and photocoagulation by infrared light which is not absorbed.

There is an increased trend toward laser systems with higher power for treating eye tissue, particularly for shortening operating times, which increases the potential risk of unwanted tissue damage.

WO 03/082162 describes a system for ophthalmological correction which has a graphical user interface for selecting collected data for the analysis with historical data and which enables instructions to be transmitted from a computer to the laser system.

US 2004/0199149 describes a method for treating eye tissue by means of laser pulses in which the surgeon creates a treatment strategy on the basis of biometric lens measurements and the refractive error to be improved. These data are used by a control program which controls the positioning of the focus, the amount of energy, pulse duration and frequency. The positioning of the focus is controlled into various areas of the lens by a scanning program in such a manner that unwanted effects on the lens tissue are prevented.

US 2004/0111083 describes a system for the computer-based planning of a refractive cornea treatment by means of pulsed laser energy, the treatment pattern being determined on the basis of a heating model of the cornea in order to avoid local overheating. In this process, in particular, a number of pulses are planned and the average pulse rate is determined on the basis of empirical data and/or thermodynamic analysis, the temperature being kept below 44 degrees in order to avoid overheating of the cornea.

The known systems enable treatment patterns to be generated which position and move the laser focus in such a manner that unwanted effects on the lens tissue (US 2004/0199149) and overheating of the cornea (US 2004/0111083), respectively, are prevented. In the treatment of the eye with femtosecond laser pulses, especially in the infrared range, there is however the risk that other eye structures which are located outside the eye tissue to be treated, particularly the iris and the retina, are damaged.

DESCRIPTION OF THE INVENTION

It is an object of the present invention to propose a device and a method for protecting tissue in the treatment of an eye with a focused pulsed laser beam generated by a laser system. In particular, it is an object of the present invention to propose a device and a method which protect eye structures located outside the tissue to be treated, such as the iris and the retina, during the treatment of an eye with a focused pulsed laser beam generated by a laser system.

According to the present invention, these aims are achieved, in particular, by the elements of the independent claims. Further advantageous embodiments are also found in the dependent claims and the description.

The device for protecting tissue in the treatment of an eye with a focused pulsed laser beam generated by a laser system is adapted for detecting operating data which define an operating area operated on by the focus of the laser beam during the treatment.

In particular, the abovementioned aims are achieved by the present invention in that the device for protecting the eye tissue is also provided with a processing module for providing control data for the laser system on the basis of input data, the input data comprising the operating data, and wherein the processing module is adapted for determining the control data by taking into consideration the light propagation in the eye in such a manner that the control data limit the time of the treatment by the focus of the laser beam at positions within the operating area in each case in such a manner that tissue damage resulting from the treatment by the laser beam is essentially prevented in eye structures located outside the operating area. The laser system is, for example, a femtolaser system. In particular, the control data are determined in such a manner that a mean irradiation intensity is reduced in the tissue and maximum temperatures in the tissue of eye structures located outside the operating area, particularly in the iris and the retina, are reduced. In particular, the control data determine movements of the focus of the laser beam within the operating area in such a manner that the mean irradiation intensity is reduced and the maximum temperatures in the tissue of eye structures located outside the operating area, particularly in the iris and the retina, are reduced. In addition or as an alternative, the control data activate and deactivate the laser beam from time to time in such a manner that the mean irradiation intensity is reduced and the maximum temperatures in the tissue of eye structures located outside the operating area, particularly in the iris and the retina, are reduced. During the generation of the control data, potential tissue damage due to overheating, phototoxicity and/or photocoagulation is taken into consideration, in particular. By providing control data which limit the time of the treatment by the focus of the laser beam at positions within the operating area, damage of tissue layers outside the operating area which absorb the irradiated energy can be avoided. By taking into consideration the light propagation in the eye, the light or the energy, respectively, can be determined which is irradiated into other eye structures located outside the operating area. Thus, control data can be provided which limit the time of the irradiation of light and thus the light absorption into these eye structures that are not to be treated (i.e. parts of the eye which do not comprise a part of the operating area) and prevent tissue damage in these eye structures. In the treatment of the cornea or the lens, for example, damage of eye structures located outside the cornea or lens, respectively, can be prevented, particularly in the iris and the retina which have a high absorption due to their high pigmentation.

In a preferred variant of the embodiment, laser parameters of the laser system are stored by the device and the control data are generated on the basis of the input data, the input data also comprising the laser parameters. The laser parameters comprise pulse energy, pulse width, maximum pulse intensity (depending on the pulse shape, the values of the pulse intensity differ with otherwise identical pulse width and pulse energy) pulse rate, wavelength, focus size, mean laser power, numeric aperture and/or scanning pattern of the laser system. Taking into consideration the laser parameters enables the control data to be provided specifically for the laser system used and thus to optimize the use of the laser energy with respect to time and energy.

In a preferred variant of the embodiment, eye dimensions are stored by the device and the control data are generated on the basis of the input data, the input data also comprising the eye dimensions. The eye dimensions define an eye model, particularly an optical geometry of the eye and comprise information about size and relative position of eye structures, the eye structures comprising the eyeball, the cornea, the lens, retina, pupil and/or iris. Taking into consideration the eye dimensions enables the control data to be provided specifically for the eye to be treated and thus to optimize the use of the laser energy with respect to time and energy.

In a variant of the embodiment, the device stores empirical data about the load limits of eye structures and the control data are generated on the basis of the input data, the input data also comprising the load limits. The empirical data comprise, for example, load limits of eye structures for various laser parameters. Storing empirical load limits enables the device to be configured in a simple manner with new empirical values.

In a variant of the embodiment, the device comprises a modeling module which is adapted for determining loads on the eye structures resulting from the treatment by the laser beam on the basis of the input data and the control data are determined on the basis of these loads and stored load limits. By modeling and calculating the expected loads on the eye structures, the control data can be adapted as accurately as possible to the risks of damage expected. In a variant, the eye model also comprises absorption coefficients associated with the eye structures, which are taken into consideration in the determination of the loads on the eye structures resulting from the treatment by the laser beam.

In a variant of the embodiment, control signals based on the control data are transmitted to the laser system. In an alternative variant of the embodiment, the control data are transmitted to the laser system for storage. Storing the control data enables the laser system to be controlled automatically on the basis of the control data previously provided by the safety device. Transmitting the control signals enables the laser system to be controlled in real time by the safety device.

In a preferred variant of the embodiment, the load data are received directly by the laser system. The direct acquisition of the operating data by the laser system provides for real-time control and monitoring of the operating process on the eye and thus an increase in safety.

In a variant of the embodiment, operating patterns and/or operating instructions based on the control data are displayed on a display, which operating patterns and/or operating instructions define a movement sequence of the focus of the laser beam during the treatment of the operating area.

Apart from the device and the method for protecting tissue in the treatment of an eye with a focused pulsed laser beam generated by a laser system, the present invention is also related to a computer program product with computer program code means for controlling one or more processors, particularly a computer program product with a computer-readable medium which comprises the computer program code means. The computer program code means control the processors in such a manner that they provide control data which are suitable for controlling a laser system in such a manner that tissue damage at eye structures located outside the operating area are essentially prevented in the treatment of an eye with a focused pulsed laser beam generated by a laser system.

BRIEF DESCRIPTION OF THE DRAWINGS

In the text which follows, an embodiment of the present invention is described by means of an example. The example of the embodiment is illustrated by the following attached figures.

APPROACHES FOR CARRYING OUT THE INVENTION

Figure 1:
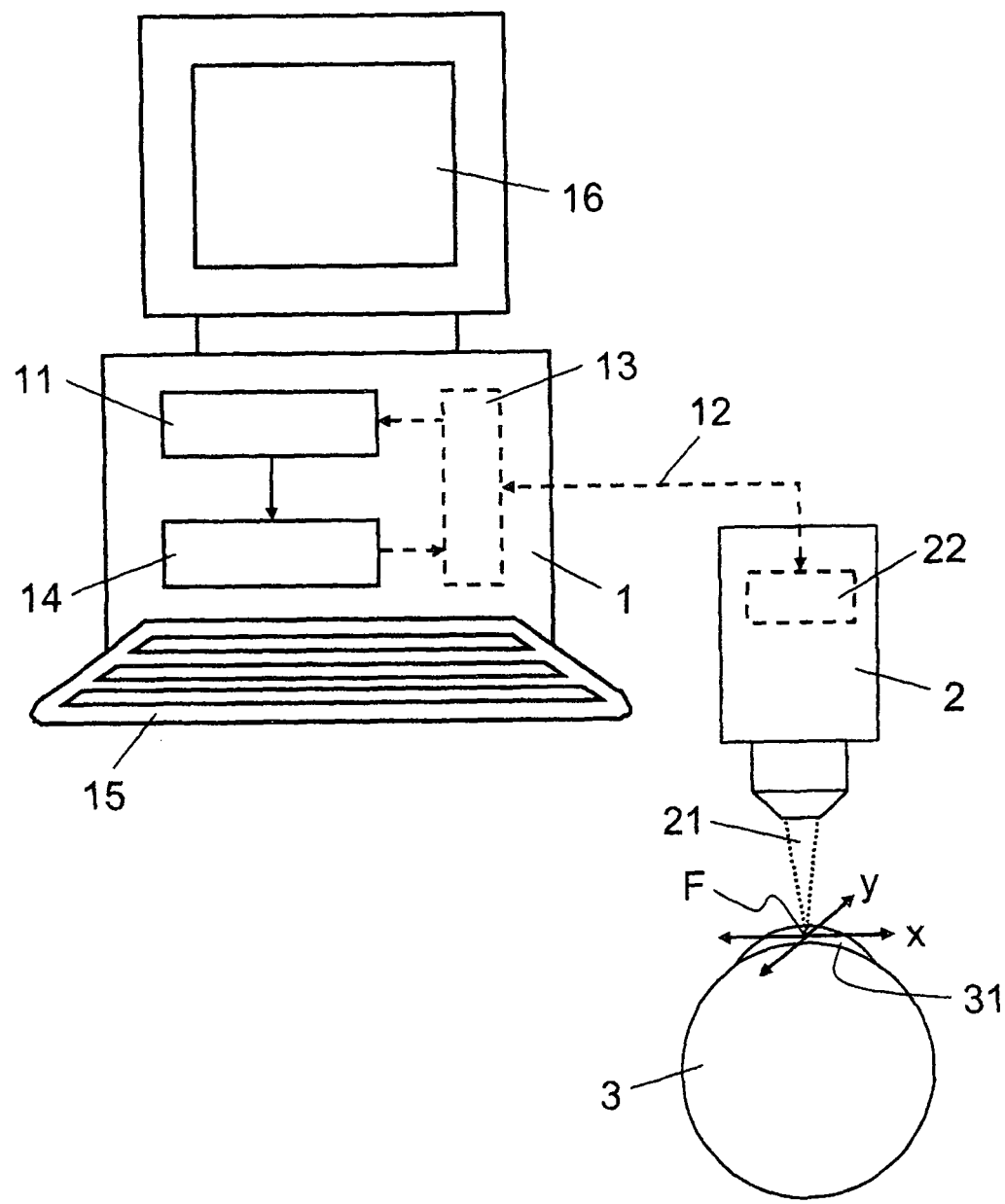
FIG. 1 shows a block diagram which diagrammatically represents a laser system in the treatment of an eye by means of a focused pulsed laser beam, and a device for protecting tissue of the eye during the treatment.

In FIG. 1, reference symbol 2 designates a laser system which is adapted for generating a focused pulsed laser beam 21 and operating on an eye 3 by means of the laser beam 21. As is shown diagrammatically in FIG. 1, the laser system 2 is adapted for moving the focus F of the laser beam 21 at least in two dimensions x, y of a (coherent or non-coherent) operating area in or on the tissue 31 of the eye 3. In a variant of the embodiment, the laser system 2 is also adapted for moving the focus F also in a third direction normal to the two dimensions x, y. The laser system 2 preferably comprises a femtolaser for generating femtosecond laser pulses which have pulse widths of typically 100 fs to 1000 fs (1 fs=$10^{-15}$ s). In a variant of the embodiment, the laser system 2 comprises a communication module 22 for the unidirectional or bidirectional data exchange with a communication module 13 of the device 1 via the communication interface 12. The communication interface 12 is, for example, a wire-connected interface, e.g. an RS-232, RS-422 or RS-485 interface, or a contactless interface, e.g. an infrared interface (e.g. IrDA) or a radio interface (e.g. Bluetooth).

In FIG. 1, reference symbol 1 designates a device for protecting the tissue 31 in the treatment of the eye 3 by means of the laser beam 21 generated by the laser system 2. The device 1 preferably comprises an operable programmable processor and associated data and program memories or another electronic logic module. The device 1 is preferably equipped with or connected to operating elements 15, e.g. a keyboard, a positioning device (computer mouse, joystick, track ball, touch pad or the like) and/or a voice control unit, and a display 16. The device 1 is constructed, for example, as a personal computer or as a specially configured electronic module. In a variant of the embodiment, the device 1 and the laser system 2 are integrated in a common housing. Apart from the communication module 13 already mentioned, the device 1 comprises a data acquisition module 11 and a processing module 14. For accessing data, the processing module 14 can be connected to the data acquisition module 11. As will be described later in more detail, the data acquisition module 11, for receiving data from the laser system 2, and the processing module 14, for transmitting data to the laser system 2, can be connected to the communication module 13. The processing module 14 and the data acquisition module 11 are operated, controlled and configured by the user via the operating elements 15 and the display 16, for example by a graphical user interface. The functional parts of the processing module 14 and of the data acquisition module 11 are preferably arranged as programmed software modules or software parts. The computer program code is a part of a computer program product and is preferably stored in the device 1 on a computer-readable data medium which is connected permanently or removably to the device 1. The expert will understand that the functional parts of the processing module 14 and of the data acquisition module 11 can also be arranged partially or completely in hardware.

Figure 2A:
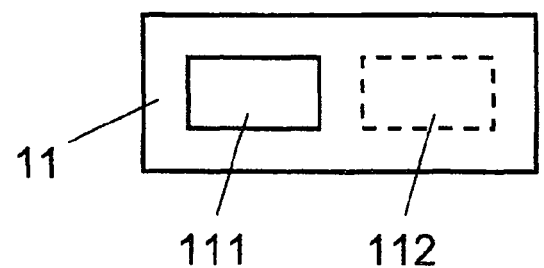
FIGS. 2a, 2b and 2c in each case show a block diagram which diagrammatically represents a possible composition of a data acquisition module of the device.
Figure 2B:
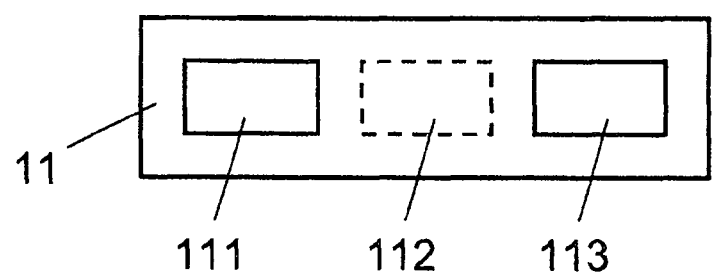
Figure 2C:
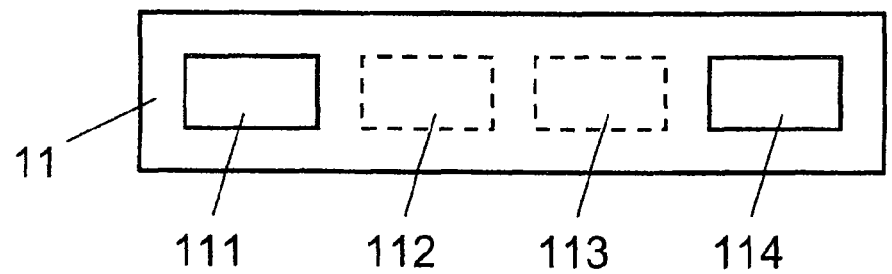

As is shown diagrammatically in FIGS. 2a, 2b and 2c, the data acquisition module 11 is configured differently depending on the variant of the embodiment. In the variants shown, the data acquisition module 11 in each case comprises an operating data module 111 for acquiring and storing operating data which define a (coherent or non-coherent) operating area which is operated on by the focus F of the laser beam 21 during the treatment. The operating data comprise predetermined operating data which are specified by the user, and/or current operating data which are acquired by the laser system 2 from the operating data module 111 via the communication interface 12. The predetermined operating data are defined by the user, for example in the form of coordinates, shape and size information and/or position information. The current operating information comprises, for example, position values (coordinates) of the focus F of the laser beam 21 which are stored by the operating data module 111 in each case correlated with time values which specify the current time of the data reception or of the position acquisition in the laser system 2. If the focus is moved at a known and constant rate, the acquisition of the time values can be omitted as long as the sequence of acquired position values is maintained.

As indicated in FIGS. 2a, 2b and 2c, the data acquisition module 11, in one variant of the embodiment, comprises in addition to the operating data module 111 a laser data module 112 for acquiring and storing laser parameters of the laser system 2. The laser parameters comprise technical characteristics of the laser system 2. The laser parameters comprise, for example, data values which specify the pulse energy, the pulse width, the pulse rate, the wavelength, the focus size, the mean laser power, the numeric aperture and/or the scanning pattern. In a variant of the embodiment, the laser parameters also comprise information about contact body, for example information about thickness, shape and/or transmission characteristic. The laser parameters are specified either by the user, read by the laser system 2 via the communication interface 12 or acquired from another external data source. The laser parameters can also be permanently programmed.

As shown diagrammatically in FIG. 2b, the data acquisition module 11, in one variant of the embodiment, comprises, in addition to the operating data module ill and the optional laser data module 112, an eye data module 113 for acquiring and storing eye dimensions. The eye dimensions comprise information about size and relative position of eye structures in the undeformed and/or deformed state (e.g. various deformed states of the eye structures depending on different contact bodies). The eye structures comprise cornea, lens, retina, pupil, eyeball and/or iris. The eye dimensions are specified either by the user, read by the laser system 2 equipped with corresponding measuring devices via the communication interface 12 or acquired from another external measuring device. Eye dimensions for a generic eye can also be permanently programmed. In one variant of the embodiment, the eye data module 113 also acquires and stores specific light absorption coefficients in each case associated with the eye structures.

As is shown diagrammatically in FIG. 2c, the data acquisition module 11, in one variant of the embodiment, comprises, in addition to the operating data module 111, the optional laser data module 112 and the optional eye data module 113, a reference data module 114 for acquiring and storing empirical data about load limits of the eye structures (which have been obtained, e.g. directly by means of the laser system) and empirical data about tissue damage. The empirical data preferably comprise load limits of eye structures for various laser parameters. The load limits of eye structures are acquired, for example, for various defined combinations of values of the laser parameters or defined configurations of the laser system 2. The load limits are specified, for example, in the form of a maximum mean irradiation intensity and/or maximum irradiation time with known irradiation. The mean irradiation intensity is specified, for example, with regard to a total operating time, over the entire operating area and/or a local operating time over a defined part area. The empirical data are specified either by the user, read by the laser system 2 via the communication interface 12 or acquired from another external data source. The load limits can also be permanently programmed.

The processing module 14 is adapted for providing control data for the laser system 2 on the basis of input data which comprise at least the operating data for determining the operating area. The control data comprise instructions for the laser system 2 and/or for the user of the laser system 2. The instructions relate, for example, to the activation/deactivation of the laser beam 21, particular settings of the laser system such as the irradiation intensity or pulse frequency, and/or the movement of the focus in a particular direction or to a particular position, respectively. The processing module 14 determines the control data in such a manner that the treatment by the focus F in the operating area is limited in time in such a manner that tissue damage in eye structures located outside the operating area is essentially prevented. When operating on the cornea or the lens, for example, tissue damage in the iris or the retina is prevented. In a variant, the processing module 14 is also adapted for determining the control data in such a manner that the focused projection of the laser pulses is limited in time in such a manner that tissue damage outside the operating area and, in particular, also in the immediate vicinity of the operating area is essentially prevented. When operating on the cornea, for example, damage at the immediately adjacent stromal tissue and/or in the epithelial tissue located above it is to be prevented. The control data are determined in such a manner that the mean irradiation intensity in the tissue is reduced and maximum temperatures in the tissue outside the operating area are reduced and are limited, for example, to defined maximum values. The control data are determined, for example, in such a manner that they determine a movement pattern for the movements of the focus within the operating area with which the mean irradiation intensity in the tissue is reduced and maximum temperatures in the tissue outside the operating area are reduced. In addition or as an alternative, the control data are determined in such a manner that they activate and deactivate the laser beam from time to time in such a manner that the mean irradiation intensity is reduced and the maximum temperatures in the tissue outside the operating area are reduced. The mean irradiation intensity is determined for the time window of a treatment in a local coherent part-operating area or for the time window of a total treatment over the entire operating area. During the generation of the control data, the processing module 14 takes into consideration potential tissue damage due to overheating, phototoxicity and/or photocoagulation. The processing module 14 receives the input data from the data acquisition module 11 and/or from the user.

Figure 3A:
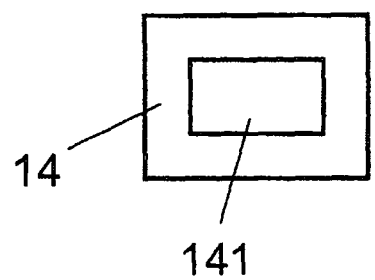
FIGS. 3a, 3b and 3c in each case show a block diagram which diagrammatically represents a possible configuration of a processing module of the device.
Figure 3B:
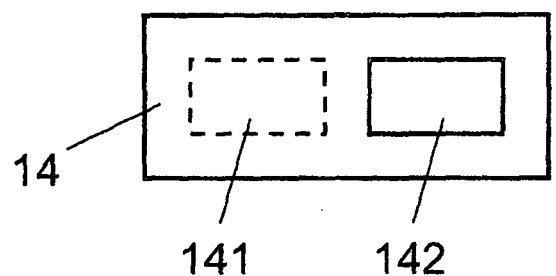
Figure 3C:
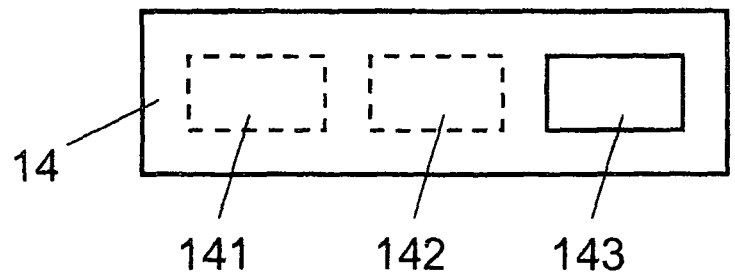

As is shown diagrammatically in FIGS. 3a, 3b and 3c, the processing module 14 is configured differently depending on the variant of the embodiment. In the simplest variant of the embodiment, the processing module 14 is adapted for providing the control data only in dependence on the operating area on the basis of the operating data independently of laser parameters, for example for a defined standard type of the laser system 2, and independently of eye dimensions, for a generic eye with average eye dimensions and light absorption coefficients. In the simplest case, predefined control data are stored correlated with different operating or movement patterns. In more flexible variants of the embodiment, the processing module 14, for providing the control data, also takes into consideration the laser parameters of the laser system 2, the eye dimensions of the eye 3, the light absorption coefficients of the various eye structures and/or the empirical data about the load limits of the eye structures. For example, predefined control data are stored correlated with different operating or movement patterns and laser parameters and/or eye dimensions, that is to say for different combinations of operating or movement patterns, laser parameters and/or eye dimensions, different predefined control data are obtained. In the most flexible variant of the embodiment, the processing module 14, as indicated in FIGS. 3a, 3b and 3c, comprises a modeling module 141 which is adapted for determining the loads on the eye structures resulting from the treatment by the laser beam 21 on the basis of the input data which, at the least, comprise the operating data. The loads on the eye structures are determined on the basis of the energy which is expected to be absorbed in the eye structures of a generic eye with average eye dimensions during the treatment of the operating area by a standard laser during a particular action time. If the data acquisition module 11 comprises a laser data module 112, the input data also comprise the laser parameters of the laser system 2 and the modeling module 141 determines the loads on the eye structures which result from the treatment of the operating area, determined by the operating data, by means of the laser system 2 determined by the laser parameters. If the data acquisition module 11 comprises an eye data module 113, the input data also comprise the eye dimensions of the eye 3 and the modeling module 141 determines the loads on the eye structures taking into consideration these eye dimensions. In the most flexible variant of the embodiment, the loads on the eye structures are determined on the basis of the energy which is expected to be absorbed in the eye structures defined by the eye dimensions during the treatment of the operating area by the laser system 2 defined by the laser parameters during a particular action time. In a variant of the embodiment, the modeling module 141 determines the loads on the eye structures by taking into consideration the empirical data about tissue damage. The modeling module 141 determines the loads on the eye structures by applying physical laws relating to light propagation, heat conduction and/or to absorption characteristics, for example by taking into consideration the individual light absorption coefficients of the various eye structures. In particular, the modeling module 141 is adapted for determining (mathematically and/or by table) the propagation of the light in the eye 3, irradiated by the laser beam 21 during the treatment. The defined standard type of the laser system 2 or a laser system 2 defined by the laser parameters is assumed. The light propagation is determined on the basis of a generic eye model having average dimensions, distances and properties (e.g. dispersion, refraction, reflection) of the eye structures or of an eye model determined by the acquired eye dimensions. In this context, the light propagation in the eye and, in particular, the light irradiated into the eye structures located outside the operating area, are determined in each case for the projection of the focused laser pulses to a focus F within the operating area. The eye model defines, for example, the proportion (e.g. a percentage) of the amount of light or energy, respectively, irradiated at a particular focus position which is irradiated into a particular eye structure and/or at a particular place of this eye structure. The load, particularly the heat load on the eye structures is determined by integrating the amount of light or energy, respectively, irradiated into the eye structures located outside the operating area by a number of laser pulses. This preferably takes into consideration the heat conduction and/or the absorption characteristic of the tissue of the eye structures. For example, when treating the cornea, the amount of light or energy, respectively, is determined which is irradiated into/onto the iris and/or retina due to the laser pulses projected into the cornea. On this basis, the heat load on the iris and the retina, respectively, is determined. For example, regional average values, maximum point values, individual point values and/or regional value distributions of the amount of light, amount of energy and/or heat loading in the eye structures are determined.

The processing module 14 determines the control data for the laser system 2 on the basis of the loads on the eye structures which are determined by the modeling module 141. For this purpose, the processing module 14 preferably takes into consideration the data, stored in the reference data module 114, about the load limits for the eye structures and/or the empirical data about tissue damage.

As is shown diagrammatically in FIG. 3b, the processing module 14, in a variant of the embodiment, comprises, in addition to the optional modeling module 141, a signaling module 142. The signaling module 142 is adapted for generating control signals on the basis of the control data and transmitting them to the laser system 2 via the communication module 13.

As is shown diagrammatically in FIG. 3c, the processing module 14, in a variant of the embodiment, comprises, in addition to the optional modeling module 141 and to the optional signaling module 142, a planning module 143. The planning module 143 is adapted for displaying, on the basis of the control data, operating patterns on the display 16 which represent the planned and/or actual (current) movement sequence of the focus F during the treatment of the operating area. In a variant of the embodiment, the planning module 143 is adapted for transmitting the control data for planned movement sequences (i.e. for planned treatments) for storage to the laser system 2 via the communication module 13. During the representation of current movement sequences, for example, corresponding control signals are also transmitted to the laser system 2 by means of the signaling module 142.

Figure 4:
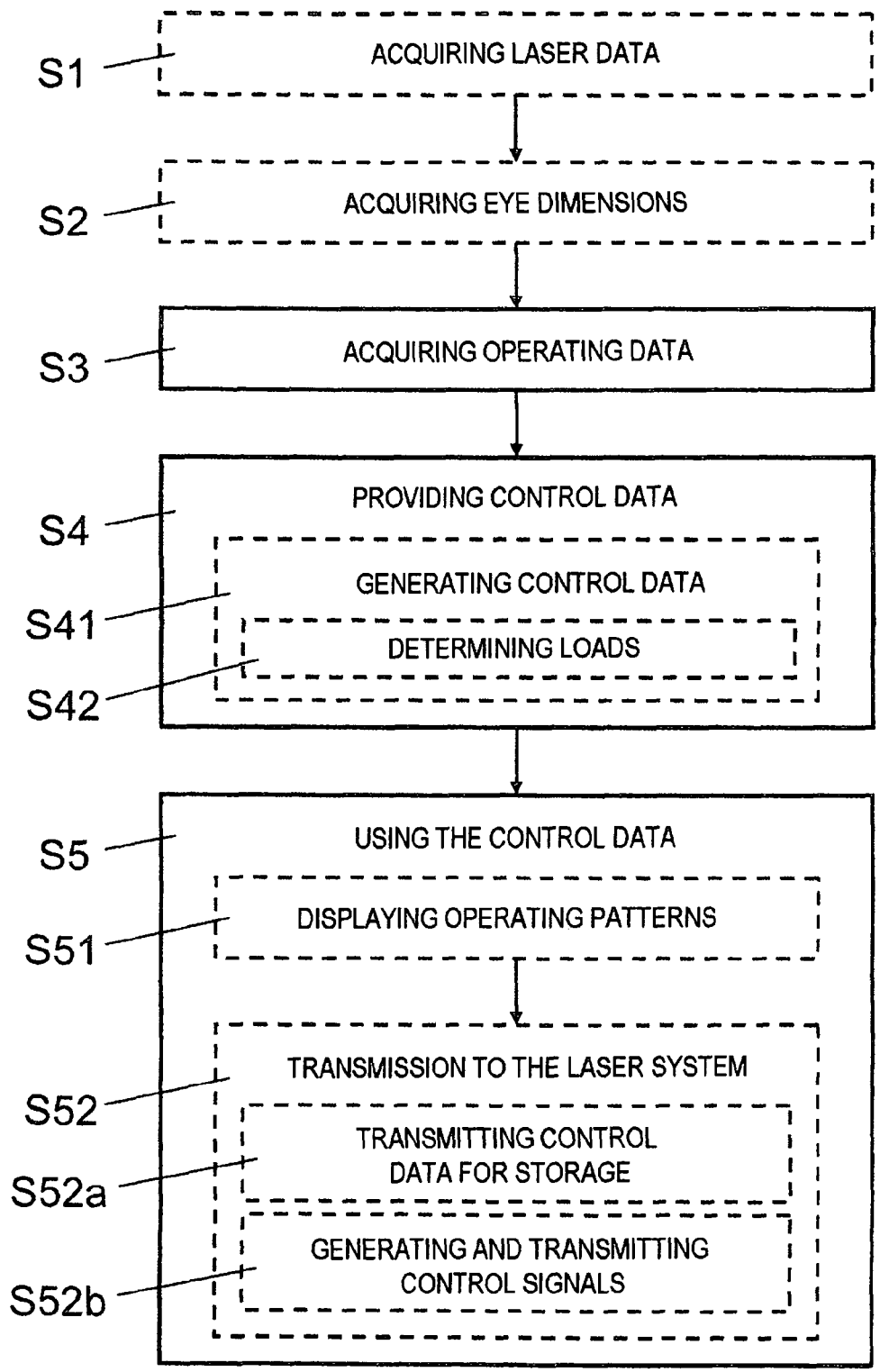
FIG. 4 shows a flowchart which diagrammatically represents possible method sequences for protecting the tissue in the treatment of the eye by the focused pulsed laser beam of the laser system.

In the sections following, possible method steps for protecting tissue 31 by means of the device 1 during the treatment of the eye 3 by the laser beam 21 are described with reference to FIG. 4.

In the optional step S1, the laser data module 112 acquires and stores the laser parameters of the laser system 2.

In the optional step S2, the eye data module 113 acquires and stores the eye dimensions of the eye 3.

In step S3, the operating data module 111 acquires and stores the current and/or predetermined planned operating data of the current or planned operating area, respectively.

In step S4, the processing module 14 provides the control data on the basis of the operating data, the laser parameters of the laser system 2, the eye dimensions of the eye 3 and/or the empirical data about the load limits of the eye structures. In the most flexible variant of the embodiment, the modeling module 141 determines the loads on the eye structures resulting from operating in accordance with the operating data in step S42, and the processing module 14 generates the control data in step S41 on the basis of these loads and the stored load limits of the eye structures.

In step S5, the control data are used by the device 1. If the device 1 is adapted as planning device or monitoring device, the control data are displayed as operating pattern and/or operating instructions on the display 16 in step S51. The operating patterns and/or operating instructions displayed determine the movement sequence of the focus F during the treatment of the operating area. In the simplest form, the control data are instructions to the user for controlling and operating the laser system 2, which can be displayed on the display, for example instructions such as stop, deactivate, or continue, activate, set and/or execute operating pattern. In particular, the monitoring device is suitable for supporting a user in the execution of a semiautomatic treatment in which the user controls the laser system manually by means of an operating element, e.g. a joystick. In a safer variant of the embodiment, the control data are transmitted to the laser system 2 in step S52 for controlling the laser system 2, for example for controlling the movement sequence of the focus F and/or the activation of the laser beam 21. For example, the movement pattern of the focus F defined by the control data is displayed on the display 16 and in step S52*a*, the control data are transmitted for storage to the laser system 2 where they control the laser system 2. If the device 1 is adapted as real-time control device, control signals are generated in step S52*b* on the basis of the control data and transmitted to the laser system 2 for controlling the laser system 2 in real time. In this variant of the embodiment, current operating data which define the operating area currently operated on are preferably also transmitted from the laser system 2 to the device 1 (feedback), e.g. a sequence of current positions. Such a feedback of the current operating data from the laser system 2 to the device 1 is also of advantage, for example, for the monitoring device described above for semiautomatic use.

The invention claimed is:

1. A system for protecting tissue in the treatment of an eye with a focused pulsed laser beam generated by a laser system, comprising one or more processors configured to implement an operating data module and a processing module:

the operating data module configured to store operating data which define shape and position of an operating area inside the tissue of the eye operated on by the focus of the laser beam during the treatment by moving the focus within the operating area inside the tissue of the eye, and the processing module configured to generate control data for the laser system on the basis of input data, the input data comprising the operating data, and wherein the processing module is configured to determine, based on an eye model defined by stored eye dimensions, the light propagation in the eye for the projection of a laser pulse onto the focus within the operating area inside the tissue of the eye, to determine, based on the eye model, the light irradiated into eye structures located outside the operating area for the projection of the laser pulse onto the focus within the operating area inside the tissue of the eye, to determine a load on the eye structures located outside the operating area from the light irradiated into the eye structures located outside the operating area, as determined based on the eye model, and to generate the control data by taking into consideration the load on the eye structures located outside the operating area in such a manner that the control data limits the time of the treatment by the focus of the laser beam at positions within the operating area inside the tissue of the eye in each case in such a manner that tissue damage resulting from the treatment by the laser beam is essentially prevented in eye structures located outside the operating area, and the processors are further configured to control the laser system using the control data.

2. The system as claimed in claim 1, which comprises a laser data module for storing laser parameters of the laser system and wherein the processing module is adapted for generating the control data on the basis of the input data, the input data also comprising the laser parameters.

3. The system as claimed in claim 1, which comprises an eye data module for storing eye dimensions and wherein the processing module is adapted for generating the control data on the basis of the input data, the input data also comprising the eye dimensions.

4. The system as claimed in claim 1, which comprises a reference data module for storing empirical data about load limits of eye structures and wherein the processing module is adapted for generating the control data on the basis of the input data, the input data also comprising the load limits.

5. The system as claimed in claim 4, wherein the empirical data comprise load limits of eye structures for various laser parameters.

6. The system as claimed in claim 1, which comprises a modeling module which is adapted for determining loads on the eye structures resulting from the treatment by the laser beam on the basis of the input data and wherein the processing module is adapted for determining the control data on the basis of these loads and stored load limits.

7. The system as claimed in claim 1, wherein the processing module is adapted for determining the control data in such a manner that a mean irradiation intensity is reduced in the tissue and maximum temperatures in the tissue of eye structures located outside the operating area are reduced.

8. The system as claimed in claim 7, wherein the control data determine movements of the focus of the laser beam within the operating area in such a manner that the mean irradiation intensity is reduced and the maximum temperatures in the tissue of eye structures located outside the operating area are reduced.

9. The system as claimed in claim 7, wherein the control data activate and deactivate the laser beam from time to time in such a manner that the mean irradiation intensity is reduced and the maximum temperatures in the tissue of eye structures located outside the operating area are reduced.

10. The system as claimed in claim 7, wherein the processing module is adapted for determining the control data in such a manner that the maximum temperatures in the tissue of the iris and the retina are reduced.

11. The system as claimed in claim 1, comprising a signaling module which can be connected to the laser system and which is adapted to transmit control signals based on the control data to the laser system.

12. The system as claimed in claim 1, wherein the operating data module can be connected to the laser system and is adapted for receiving the operating data directly from the laser system.

13. The system as claimed in claim 1, wherein a planning module which is adapted for displaying operating patterns and/or operating instructions based on the control data on a display, which operating patterns and/or operating instructions define a movement sequence of the focus of the laser beam during the treatment of the operating area.

14. The system as claimed in claim 13, wherein the planning module can be connected to the laser system and is adapted for transmitting the control data to the laser system for storage.

15. The system as claimed in claim 2, wherein the laser parameters comprise at least one value from pulse energy, pulse width, pulse rate, wavelength, focus size, mean laser power, numeric aperture and scanning pattern.

16. The system as claimed in claim 3, wherein the eye dimensions comprise information about size and relative position of eye structures, the eye structures comprising at least one of cornea, lens, retina, pupil, eyeball and iris.

17. The system as claimed in claim 1, wherein the laser beam is a focused pulsed laser beam generated by a femtolaser system.

18. A computer program product comprising a non-transitory computer-readable medium storing computer program code means for controlling one or more processors of a device, in such a manner that the processors acquire operating data which define an operating area inside the tissue of an eye to be operated on by the focus of a pulsed laser beam generated by a laser system during the treatment of an eye by moving the focus within the operating area inside the tissue of the eye, and provide control data for the laser system on the basis of input data, the input data comprising the operating data, wherein the processors determine a light propagation in the eye based on an eye model defined by stored eye dimensions for the projection of a laser pulse onto the focus within the operating area inside the tissue of the eye, the processors determine, based on the eye model, the light irradiated into eye structures located outside the operating area, the processors determine a load on the eye structures located outside the operating area from the light irradiated into the eye structures located outside the operating area, as determined based on the eye model, the processors generate the control data by taking into consideration the load on the eye structures located outside the operating area in such a manner that the control data limits the time of a treatment by the focus of the laser beam at positions within the operating area inside the tissue of the eye in each case in such a manner that tissue damage resulting from the treatment by the laser beam is essentially prevented in eye structures located outside the operating area, and the processors control the laser system using the control data.

19. A system for protecting tissue in the treatment of an eye with a focused pulsed laser beam generated by a laser system, comprising one or more processors configured to implement an operating data module and a processing module:
the operating data module configured to acquire operating data which define an operating area inside the tissue of the eye operated on by the focus of the laser beam during the treatment by moving the focus within the operating area inside the tissue of the eye, and
the processing module for providing control data for the laser system on the basis of input data, the input data comprising the operating data, and
wherein the processing module is configured to determine the control data by taking into consideration the light propagation in the eye based on an eye model defined by stored eye dimensions for the projection of a laser pulse onto the focus within the operating area inside the tissue of the eye, to determine, based on the eye model, the light irradiated into eye structures located outside the operating area for the projection of the laser pules onto the focus within the operating area inside the tissue of the eye, to determine a load on the eye structures located outside the operating area from the light irradiated into the eye structures located outside the operating area, as determined based on the eye model, and to generate the control data by taking into consideration the load on the eye structures located outside the operating area in such a manner that the control data limits the time of the treatment by the focus of the laser beam at positions within the operating area inside the tissue of the eye in each case in such a manner that tissue damage resulting from the treatment by the laser beam is essentially prevented in eye structures located outside the operating area, and
the processors are further configured to control the laser system using the control data.

20. The system as claimed in claim 1, wherein the processing module is adapted for taking into consideration potential tissue damage due to overheating, phototoxicity and/or photocoagulation when generating the control data.

21. A system for protecting tissue in the treatment of an eye with a focused laser beam generated by a laser system, comprising one or more processors configured to implement an operating data module and a processing module:
the operating data module configured to acquire operation data which define an operating area inside the tissue of the eye operated on by the focus of the laser beam during the treatment by moving the focus within the operating area inside the tissue of the eye, and
the processing module for providing control data for the laser system on the basis of input data, the input data comprising the operating data, and
wherein the processing module is configured to determine the light propagation in the eye based on an eye model defined by stored eye dimensions, for the projection of a laser beam onto the focus within the operating area inside the tissue of the eye, to determine the light irradiated into eye structures located outside the operating area, to determine a load on the eye structures located outside the operating area from the light irradiated into the eye structures located outside the operating area, and to determine the control data by taking into consideration the load on the eye structures located outside the operating area in such a manner that the control data limits the time of the treatment by the focus of the laser beam at positions within the operating area inside the tissue of the eye in each case in such a manner that tissue damage resulting from the treatment by the laser beam is essentially prevented in eye structures located outside the operating area, and the processors are further configured to control the laser system using the control data.

* * * * *